(12) United States Patent
Perkins et al.

(10) Patent No.: US 11,324,582 B2
(45) Date of Patent: May 10, 2022

(54) DOCKING GRAFT FOR PLACEMENT OF PARALLEL DISTALLY EXTENDING GRAFTS ASSEMBLY AND METHOD

(71) Applicant: Medtronic Vascular, Inc., Santa Rosa, CA (US)

(72) Inventors: Keith Perkins, Santa Rosa, CA (US); Mark Stiger, Santa Rosa, CA (US); Travis Rowe, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 51 days.

(21) Appl. No.: 16/585,722

(22) Filed: Sep. 27, 2019

(65) Prior Publication Data
US 2021/0093437 A1    Apr. 1, 2021

(51) Int. Cl.
*A61F 2/07* (2013.01)
*A61F 2/962* (2013.01)
*A61F 2/06* (2013.01)

(52) U.S. Cl.
CPC .............. *A61F 2/07* (2013.01); *A61F 2/962* (2013.01); *A61F 2002/061* (2013.01); *A61F 2002/075* (2013.01); *A61F 2210/0014* (2013.01)

(58) Field of Classification Search
CPC ...... A61F 2/07; A61F 2/962; A61F 2002/061; A61F 2002/075; A61F 2210/0014; A61F 2250/0039; A61F 2002/065; A61F 2002/067
See application file for complete search history.

(56) References Cited

U.S. PATENT DOCUMENTS

| 8,545,549 | B2 | 10/2013 | Hartley et al. |
| 8,702,791 | B2 | 4/2014 | Kelly |
| 8,734,504 | B2 | 5/2014 | Kelly |

(Continued)

FOREIGN PATENT DOCUMENTS

| EP | 2775958 A1 | 5/2013 |
| WO | 2018031632 A1 | 2/2018 |

(Continued)

OTHER PUBLICATIONS

PCT/US2020/051899, The International Search Report and the Written Opinion of the International Searching Authority, dated Dec. 4, 2020, 14 pages.

*Primary Examiner* — Yashita Sharma
*Assistant Examiner* — Jared Klar Rovira
(74) *Attorney, Agent, or Firm* — Innovation Counsel LLP (57) ABSTRACT

The techniques of this disclosure generally relate to an assembly including a docking graft. The docking graft includes a main graft defining a main lumen, a first internal lumen within the main lumen, a second internal lumen within the main lumen, and a main docking lumen within the main lumen. The first and second internal lumens are configured to receive first and second bridging stent graft therein. The main docking lumen is configured to receive a tube graft therein. The first internal lumen, the second internal lumen, and the main docking lumen being parallel to one another and extending an entire length of the docking graft when the docking graft is in a relaxed configuration. The docking graft forms the foundation, or anchor device, for attachment of the first bridging stent graft, the second bridging stent graft, and the tube graft within the aorta.

15 Claims, 10 Drawing Sheets

(56) References Cited

U.S. PATENT DOCUMENTS

| | | |
|---|---|---|
| 9,011,517 B2 | 4/2015 | Hartley et al. |
| 9,101,456 B2 | 8/2015 | Hartley et al. |
| 9,283,068 B2 | 3/2016 | Kelly |
| 9,393,102 B2 | 7/2016 | Kelly |
| 9,592,112 B2 | 3/2017 | Arbefeuille et al. |
| 9,861,505 B2 | 1/2018 | Khoury |
| 9,949,818 B2 | 4/2018 | Kelly |
| 9,980,832 B2 | 5/2018 | Kelly |
| 9,993,330 B2 | 6/2018 | Roeder |
| 10,231,822 B2 | 3/2019 | Hartley |
| 2013/0274861 A1 * | 10/2013 | Kelly ........................ A61F 2/95 623/1.13 |
| 2016/0287376 A1 | 10/2016 | Kelly |
| 2016/0324626 A1 | 11/2016 | Kelly |
| 2016/0367353 A1 | 12/2016 | Kelly |
| 2017/0319359 A1 | 11/2017 | Mehta |
| 2018/0235786 A1 | 8/2018 | Kelly |
| 2018/0243076 A1 | 8/2018 | Greenberg et al. |
| 2018/0325653 A1 | 11/2018 | Kelly |

FOREIGN PATENT DOCUMENTS

| | | | |
|---|---|---|---|
| WO | 2018091442 | 5/2018 | |
| WO | 2019101079 A1 | 5/2019 | |
| WO | WO-2019101079 A1 * | 5/2019 | ............... A61F 2/82 |

* cited by examiner

DOCKING GRAFT FOR PLACEMENT OF PARALLEL DISTALLY EXTENDING GRAFTS ASSEMBLY AND METHOD

FIELD

The present technology is generally related to an intra-vascular device and method. More particularly, the present application relates to a device for treatment of intra-vascular diseases.

BACKGROUND

Aneurysms, dissections, penetrating ulcers, intramural hematomas and/or transections may occur in blood vessels, and most typically occur in the aorta and peripheral arteries. The diseased region of the aorta may extend into areas having vessel bifurcations or segments of the aorta from which smaller "branch" arteries extend.

The diseased region of the aorta can be bypassed by use of a stent-graft placed inside the vessel spanning the diseased portion of the aorta, to seal off the diseased portion from further exposure to blood flowing through the aorta.

The use of stent-grafts to internally bypass the diseased portion of the aorta is not without challenges. In particular, care must be taken so that critical branch arteries are not covered or occluded by the stent-graft yet the stent-graft must seal against the aorta wall and provide a flow conduit for blood to flow past the diseased portion.

SUMMARY

The techniques of this disclosure generally relate to an assembly including a docking graft. The docking graft includes a main graft defining a main lumen, a first internal lumen within the main lumen, a second internal lumen within the main lumen, and a main docking lumen within the main lumen. The first internal lumen is configured to receive a first bridging stent graft therein and the second internal lumen is configured to receive a second bridging stent graft therein. The main docking lumen is configured to receive a tube graft therein. The first internal lumen, the second internal lumen, and the main docking lumen are parallel to one another and extend an entire length of the docking graft from a proximal end of the docking graft to a distal end of the docking graft when the docking graft is in a relaxed (unstressed) configuration. The docking graft forms the foundation, or anchor device, for attachment of the first bridging stent graft, the second bridging stent graft, and the tube graft within the aorta.

In one aspect, the present disclosure provides an assembly including a docking graft. The docking graft includes a main graft defining a main lumen, a first internal sleeve defining a first internal lumen within the main lumen, and a second internal sleeve defining a second internal lumen within the main lumen. The main lumen, the first internal lumen, and the second internal lumen are parallel to one another and extend an entire length of the docking graft from a proximal end of the docking graft to a distal end of the docking graft when the docking graft is in a relaxed configuration.

In yet another aspect, the present disclosure provides a method including deploying a docking graft within the ascending aorta. The docking graft includes a main graft defining a main lumen, a first internal lumen within the main lumen, a second internal lumen within the main lumen, and a main docking lumen within the main lumen. A first bridging stent graft is deployed within the first internal lumen, a second bridging stent graft is deployed within the second internal lumen, and a tube graft is deployed within the main docking lumen. The first bridging stent graft, the second bridging stent graft, and the tube graft are parallel to one another within the docking graft and extend distally from the docking graft.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
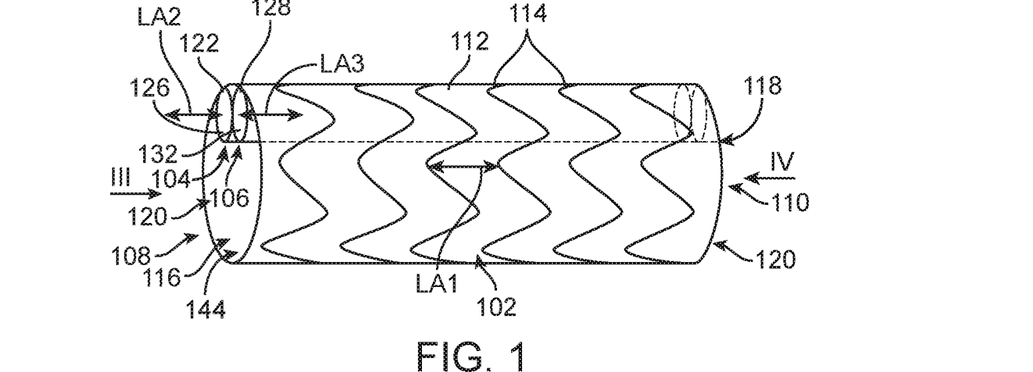
FIG. 1 is a side perspective view of a docking graft in accordance with one embodiment.
Figure 2:
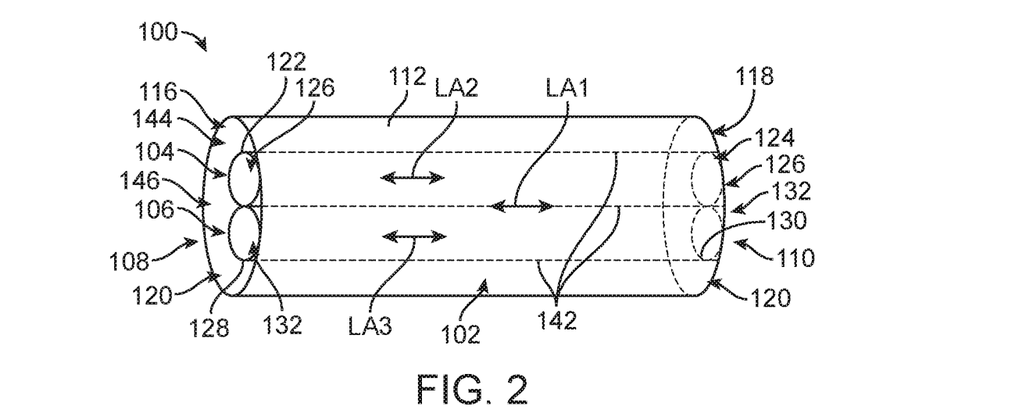
FIG. 2 is a top perspective view of the docking graft of FIG. 1 in accordance with one embodiment.

FIG. 1 is a side perspective view of a docking graft 100 in accordance with one embodiment. FIG. 2 is a top perspective view of docking graft 100 of FIG. 1 in accordance with one embodiment. Docking graft 100, sometimes called a prosthesis and/or a trifurcating device, includes a main graft 102, a first internal sleeve 104, and a second internal sleeve 106. Docking graft 100 includes a proximal end 108 and a distal end 110.

As used herein, the proximal end of a prosthesis such as docking graft 100 is the end closest to the heart via the path of blood flow whereas the distal end is the end furthest away from the heart during deployment. In contrast and of note, the distal end of the catheter is usually identified to the end that is farthest from the operator/handle while the proximal end of the catheter is the end nearest the operator/handle.

For purposes of clarity of discussion, as used herein, the distal end of the catheter is the end that is farthest from the operator (the end furthest from the handle) while the distal end of docking graft 100 is the end nearest the operator (the end nearest the handle), i.e., the distal end of the catheter and the proximal end of docking graft 100 are the ends furthest from the handle while the proximal end of the catheter and the distal end of docking graft 100 are the ends nearest the handle. However, those of skill in the art will understand that depending upon the access location, docking graft 100 and the delivery system descriptions may be consistent or opposite in actual usage.

Main graft 102 includes graft material 112 and one or more circumferential stents 114 coupled to graft material 112. Graft material 112 may be any suitable graft material, for example and not limited to, woven polyester, DACRON® material, expanded polytetrafluoroethylene, polyurethane, silicone, electro spun materials, or other suitable materials.

Circumferential stents 114 may be coupled to graft material 112 using stitching or other means. In the embodiment shown in FIG. 1, circumferential stents 114 are coupled to an outside surface of graft material 112. However, circumferential stents 114 may alternatively be coupled to an inside surface of graft material 112. Circumferential stents 114 are not illustrated in FIG. 2 to allow visualization of sleeves 104, 106.

Although shown with a particular number of circumferential stents 114, in light of this disclosure, those of skill in the art will understand that main graft 102 may include a greater or smaller number of stents 114, e.g., depending upon the desired length of main graft 102 and/or the intended application thereof.

Circumferential stents 114 may be any stent material or configuration. As shown, circumferential stents 114, e.g., self-expanding members, are preferably made from a shape memory material, such as nickel-titanium alloy (nitinol), and are formed into a zig-zag configuration. The configuration of circumferential stents 114 is merely exemplary, and circumferential stents 114 may have any suitable configuration, including but not limiting to a continuous or non-continuous helical configuration. In another embodiment, circumferential stents 114 are balloon expandable stents.

Further, main graft 102 includes a proximal opening 116 at proximal end 108 of docking graft 100, a distal opening 118 at distal end 110 of docking graft 100, and a longitudinal axis LA1. A lumen 120, sometimes called a main lumen, is defined by graft material 112, and generally by main graft 102. Lumen 120 extends generally parallel to longitudinal axis LA1 and between proximal opening 116 and distal opening 118 of main graft 102. Graft material 112 is cylindrical having a substantially uniform diameter in this embodiment. However, in other embodiments, graft material 112 varies in diameter.

Figure 3:
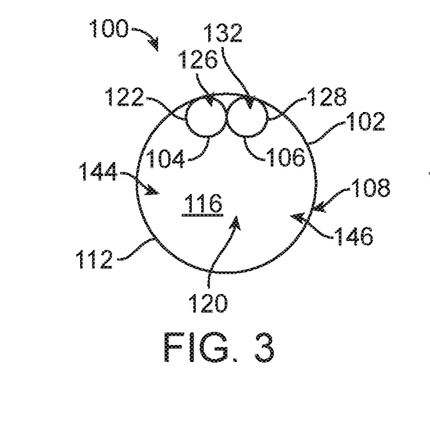
FIG. 3 is a plan view of a proximal end of the docking graft along the line III of FIG. 1 in accordance with one embodiment.
Figure 4:
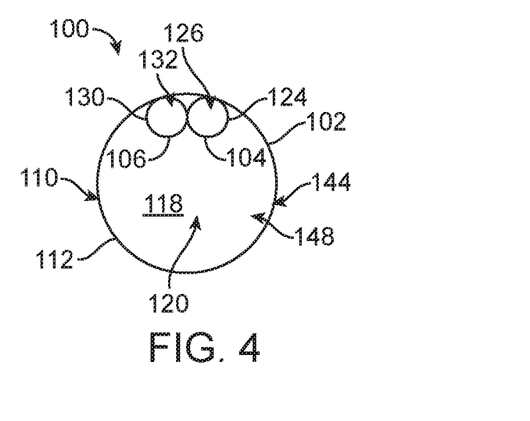
FIG. 4 is a plan view of a distal end of the docking graft along the line IV of FIG. 1 in accordance with one embodiment.

FIG. 3 is a plan view of proximal end 108 of docking graft 100 along the line III of FIG. 1 in accordance with one embodiment. FIG. 4 is a plan view of distal end 110 of docking graft 100 along the line IV of FIG. 1 in accordance with one embodiment.

Referring to FIGS. 1-4 together, first internal sleeve 104 and second internal sleeve 106 are located within main graft 102, i.e., are attached to the inner surface of graft material 112 and generally of main graft 102. Sleeves 104, 106 are located within lumen 120 of main graft 102.

First internal sleeve 104 includes a proximal opening 122 at proximal end 108 of docking graft 100, a distal opening 124 at distal end 110 of docking graft 100, and a longitudinal axis LA2. A lumen 126, sometimes called a first internal lumen 126, is defined by first internal sleeve 104. Lumen 126 extends generally parallel to longitudinal axis LA2 and between proximal opening 122 and distal opening 124 of first internal sleeve 104.

Similarly, second internal sleeve 106 includes a proximal opening 128 at proximal end 108 of docking graft 100, a distal opening 130 at distal end 110 of docking graft 100, and a longitudinal axis LA3. A lumen 132, sometimes called a second internal lumen 132, is defined by second internal sleeve 106. Lumen 132 extends generally parallel to longitudinal axis LA3 and between proximal opening 128 and distal opening 130 of second internal sleeve 106.

In accordance with this embodiment, longitudinal axes LA1, LA2, and LA3 are parallel to one another. Generally, lumens 120, 126, 132 of main graft 102, first internal sleeve 104, and second internal sleeve 106 are parallel to one another and extend the entire length of docking graft 100 between proximal end 108 and distal end 110 when docking graft 100 is in a relaxed (unstressed) configuration.

Figure 5:
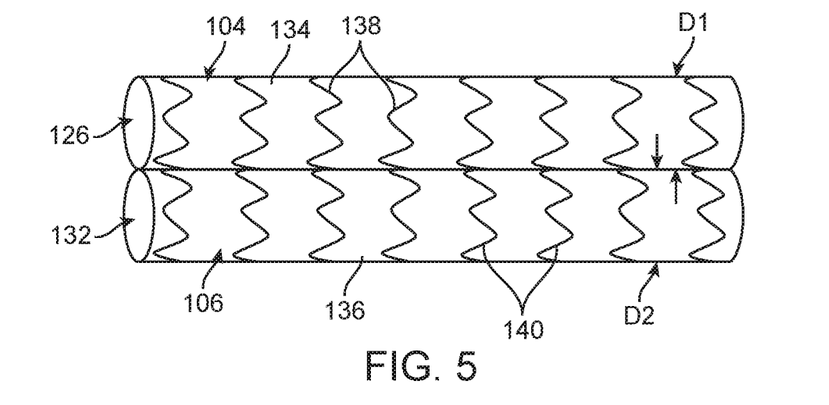
FIG. 5 is a top perspective view of sleeves of the docking graft in accordance with one embodiment.

FIG. 5 is a top perspective view of sleeves 104, 106 of docking graft 100 in accordance with one embodiment. Referring to FIGS. 1-5 together, sleeves 104, 106 include graft materials 134, 136 and one or more stents 138, 140, respectively. Graft materials 134, 136 are the same or similar to graft material 112 as discussed above. Further, stents 138, 140 are the same or similar to stents 114 as discussed above.

Graft materials 134, 136 define lumens 126, 132 of sleeves 104, 106, respectively. Stents 138, 140 insure that lumens 126, 132 remain open and accessible for docking of branch grafts therein as discussed further below.

Graft material 134 and generally first internal sleeve 104 is cylindrical having a substantially uniform diameter D1 in this embodiment. However, in other embodiments, graft material 134 and generally first internal sleeve 104 varies in diameter.

Similarly graft material 136 and generally second internal sleeve 106 is cylindrical having a substantially uniform diameter D2 in this embodiment. However, in other embodiments, graft material 136 and generally second internal sleeve 106 varies in diameter.

In accordance with this embodiment, diameters D1 and D2 are equal, although diameter D1 is greater or less than diameter D2 in other embodiments, e.g., depending upon the branch graft to be located within sleeves 104, 106 and the vessels to be perfused therethrough.

In accordance with this embodiment, internal sleeves 104, 106 abut one another, e.g., are attached, along the entire lengths of internal sleeves 104, 106. Internal sleeves 104, 106 are attached to graft material 112, and generally to main graft 102, by an attachment means 142. Attachment means 142 includes stitching, adhesive, or other suitable attachment means.

In accordance with this embodiment, lumens 126, 132 are entirely defined by graft materials 134, 136. Stated another way, graft materials 134, 136 are cylindrical and completely surround lumens 126, 132. However, in other embodiments such as that discussed below with reference to FIG. 6, graft materials 124, 136 in combination with graft material 112 define lumens 126, 132.

Figure 6:
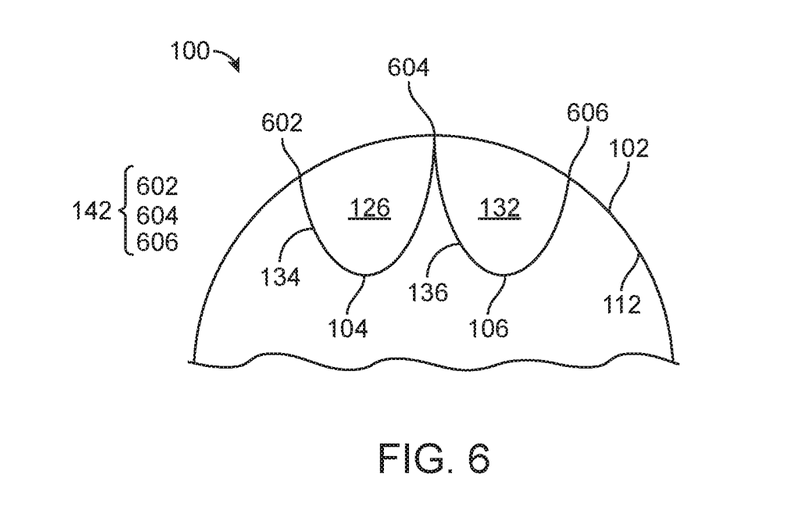
FIG. 6 is a partial cross-sectional view in a direction perpendicular to a longitudinal axis of a main graft of the docking graft of FIGS. 1-2 in accordance with another embodiment.

FIG. 6 is a partial cross-sectional view in a direction perpendicular to longitudinal axis LA1 of main graft 102 of docking graft 100 of FIGS. 1-2 in accordance with another embodiment. Referring now to FIGS. 1-4, and 6 together, first internal sleeve 104 in combination with main graft 102 define lumen 126. More particularly, graft material 134 of first internal sleeve 104 is attached by attachment means 142 to graft material 112 of main graft 102 to define lumen 126. Similarly, graft material 136 of second internal sleeve 106 is attached by attachment means 142 to graft material 112 of main graft 102 to define lumen 132.

For example, graft materials 134, 136 are portions of a single piece of graft material that is attached by attachment means 142, e.g., sewn, to graft material 112 along three seams 602, 604, 606 that extend in a direction parallel to longitudinal axes LA1, LA2, and LA3 and between proximal end 108 and distal end 110 of docking graft 100. Accordingly, lumen 126 is defined by a portion of graft material 112 between seams 602, 604 and graft material 134 between seams 602, 604. Similarly, lumen 132 is defined by a portion of graft material 112 between seams 604, 606 and graft material 136 between seams 604, 606.

Referring again to FIGS. 1-4 together, first internal sleeve 104 including lumen 126 and second internal sleeve 106 including lumen 132 are located within lumen 120 of main graft 102. The remaining volume of lumen 120 of main graft 102 that is not occupied by sleeves 104, 106 is a main docking channel 144, sometimes called a main docking lumen 144. More particularly, main docking channel 144 is the portion of lumen 120 of main graft 102 that is not occupied by sleeves 104, 106. In other words, main docking channel 144 is defined by the inner surface of graft material 112 and the outer surfaces of sleeves 104, 106.

More particularly, lumen 120 of main graft 102 is divided into, or formed of, lumens 126, 132 and 144. Lumens 126, 132, 144 are parallel to one another and extend the entire length of docking graft 100.

Accordingly, main docking channel 144 extends the entire length of docking graft 100 from proximal end 108 to distal end 110. Main docking channel 144 has a proximal opening 146 at proximal end 108 that is the area of proximal opening 116 of graft material 112 minus the areas of proximal openings 122, 128 of sleeves 104, 106. Further, main docking channel 144 has a distal opening 148 at distal end 108 that is the area of distal opening 118 of graft material 112 minus the areas of distal openings 124, 130 of sleeves 104, 106.

As discussed further below, main docking channel 144 is a channel for docking of a main tube graft therein. Further, lumens 126, 132 of internal sleeves 104, 106 are channels for docking of branch stent grafts therein and so are sometimes called docking channels 126, 132. Generally, docking graft 100 is a docking device for attachment and securement in the aorta of a tube graft and branch stent grafts as discussed below.

Figure 7:
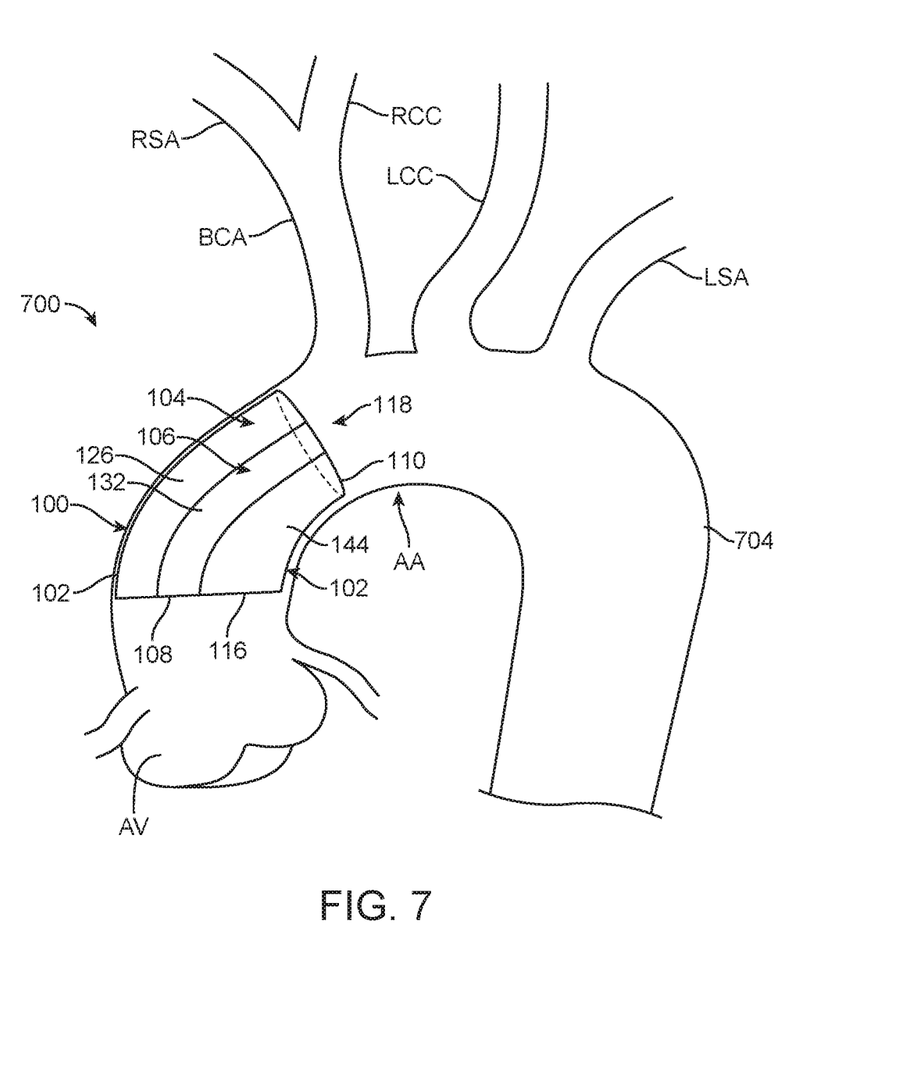
FIG. 7 is a vessel assembly including the docking graft after deployment in accordance with one embodiment.

FIG. 7 is a vessel assembly 700 including docking graft 100 after deployment in accordance with one embodiment. Referring to FIG. 7, the thoracic aorta 704 has numerous arterial branches. The arch AA of the aorta 704 has three major branches extending therefrom, all of which usually arise from the convex upper surface of the arch AA. The brachiocephalic artery BCA originates anterior to the trachea. The brachiocephalic artery BCA divides into two branches, the right subclavian artery RSA (which supplies blood to the right arm) and the right common carotid artery RCC (which supplies blood to the right side of the head and neck).

The left common carotid artery LCC arises from the arch AA of the aorta 704 just to the left of the origin of the brachiocephalic artery BCA. The left common carotid artery LCC supplies blood to the left side of the head and neck. The third branch arising from the aortic arch AA, the left subclavian artery LSA, originates behind and just to the left of the origin of the left common carotid artery LCC and supplies blood to the left arm. The left subclavian artery LSA and the left common carotid artery LCC are distal to the brachiocephalic artery BCA and are sometimes called aortic branch arteries distal of the brachiocephalic artery BCA.

However, a significant proportion of the population has only two great branch vessels coming off the aortic arch AA while others have four great branch vessels coming of the aortic arch AA. Accordingly, although a particular anatomical geometry of the aortic arch AA is illustrated and discussed, in light of this disclosure, those of skill in the art will understand that the geometry of the aortic arch AA has anatomical variations and that the various structures as disclosed herein would be modified accordingly.

Aneurysms, dissections, penetrating ulcers, intramural hematomas and/or transections, generally referred to as a diseased region of the aorta 704, may occur in the aorta arch AA and the peripheral arteries BCA, LCC, LSA. For example, thoracic aortic aneurysms include aneurysms present in the ascending thoracic aorta, the aortic arch AA, and one or more of the branch arteries BCA, LCC, LSA that emanate therefrom. Thoracic aortic aneurysms also include aneurysms present in the descending thoracic aorta and branch arteries that emanate therefrom. Accordingly, the aorta 704 as illustrated in FIG. 7 has a diseased region similar to any one of those discussed above which will be bypassed and excluded using docking graft 100 as discussed below.

Docking graft 100 is deployed into aorta 704, e.g., via femoral access. For example, to deploy docking graft 100, a guide wire is introduced via femoral access, i.e., is inserted into the femoral artery and routed up through the abdominal aorta, and into the thoracic aorta.

A delivery system including docking graft 100 is introduced via femoral access and is advanced into the ascending aorta 704 over the guidewire. The delivery system is positioned at the desired location such that the position of docking graft 100 is in the ascending aorta near the aortic valve AV. Docking graft 100 is then deployed from the delivery system, e.g., by removal of a sheath constraining docking graft 100. In another embodiment, docking graft 100 is delivered via supra-aortic access.

Main graft 102 is located and fixed within aorta 704 such that distal end 110 is proximal of the brachiocephalic artery BCA. Accordingly, blood flow enters proximal opening 116 of main graft 102, flows through lumen 120 of main graft 102 (including through lumens 126, 132), and exits distal opening 118 of main graft 102 and into aorta 704 thus perfusing the distal territories.

In accordance with this embodiment, docking graft 100 is deployed such sleeves 104, 106 are located along the convex upper surface of the arch AA. In FIG. 7, docking channels 126, 132, 144 are illustrated in a side by side arrangement along the convex upper surface of arch AA for clarity of illustration. Once deployed, docking graft 100 including main graft 102, internal sleeves 104, 106, and main docking channel 144 assume the shape of aorta 704 by the flexible design of docking graft 100.

Figure 8:
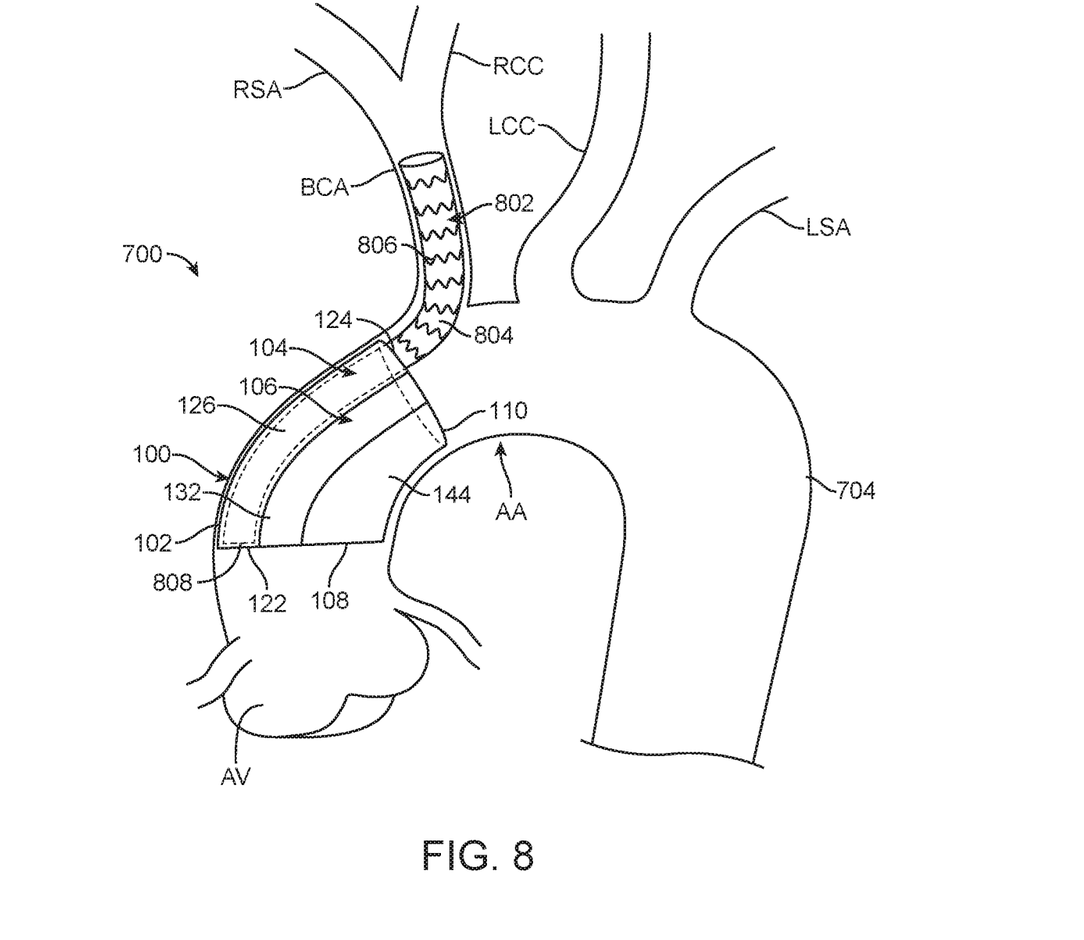
FIG. 8 is a cross-sectional view of the vessel assembly of FIG. 7 at a later stage during deployment of a bridging stent graft in accordance with one embodiment.

FIG. 8 is a cross-sectional view of vessel assembly 700 of FIG. 7 at a later stage during deployment of a first bridging stent graft 802, sometimes called a bridging stent, in accordance with one embodiment. Referring now to FIG. 8, bridging stent graft 802 is located within internal sleeve 104, i.e., within docking channel 126, and the brachiocephalic artery BCA. More particularly, bridging stent graft 802 self-expands (or is balloon expanded) to be anchored within internal sleeve 104 and the brachiocephalic artery BCA.

Bridging stent graft 802 includes graft material 804 and one or more circumferential stents 806. Graft material 804 includes any one of the graft materials as discussed above in relation to graft material 112. In addition, circumferential stents 806 are similar or identical to circumferential stents 114 as discussed above.

In one embodiment, bridging stent graft 802 is deployed via supra aortic access. For example, to deploy bridging stent graft 802, a guide wire is introduced through the right subclavian artery RSA, and advanced into distal opening 124 of internal sleeve 104.

A delivery system including bridging stent graft 802 is introduced via supra aortic access and is advanced into the brachiocephalic artery BCA and internal sleeve 104 over the guidewire. Bridging stent graft 802 is then deployed from the delivery system, e.g., by removal of a sheath constraining bridging stent graft 802.

In one embodiment, a proximal end 808 of bridging stent graft 802 is adjacent or distal of proximal opening 122 of internal sleeve 104. Accordingly, bridging stent graft 802 overlaps the entire length of docking graft 100 insuring good overlap and seal between bridging stent graft 802 and internal sleeve 104. However, in other embodiments, bridging stent graft 802 does not overlap the entire length of docking graft 100, but has sufficient overlap to insure adequate sealing. Bridging stent graft 802 is co-axial with internal sleeve 104 in accordance with this embodiment.

Upon deployment of bridging stent graft 802, blood flow into internal sleeve 104, i.e., proximal opening 122, is bridged and passed into the brachiocephalic artery BCA through bridging stent graft 802. As bridging stent graft 802 is deploy via supra aortic access, perfusion of brachiocephalic artery BCA is immediate and reliable thus minimizing the complexity of the procedure and the associated risks.

Figure 9:
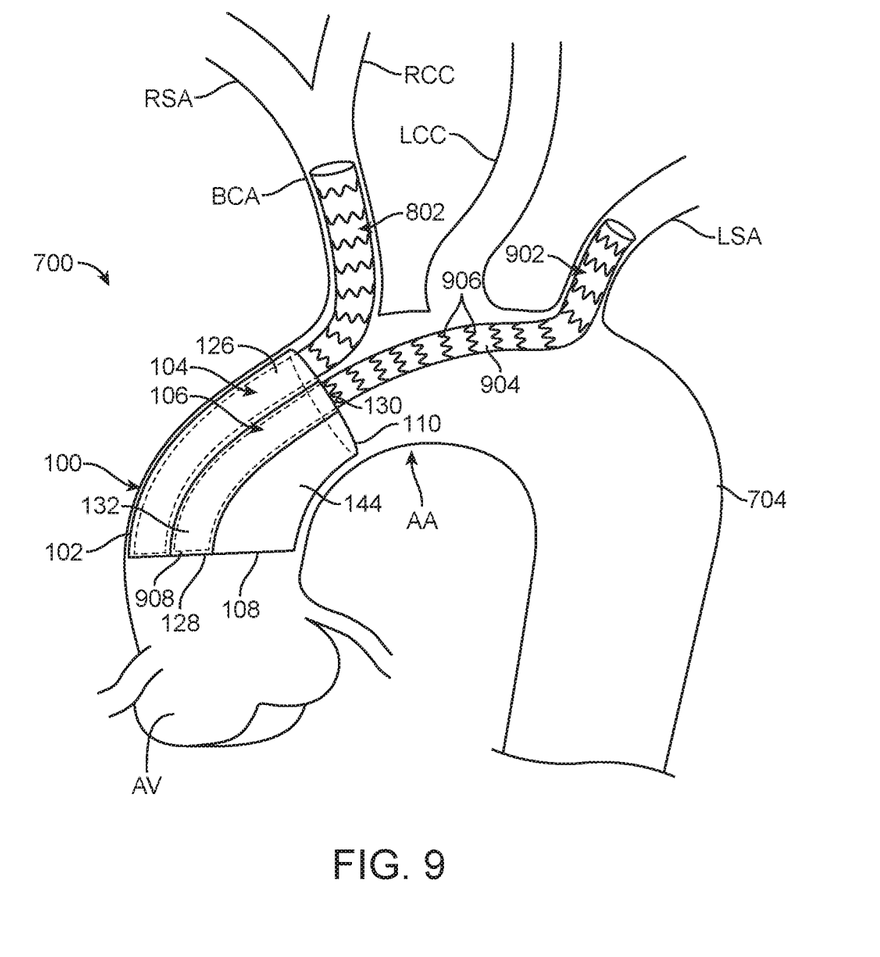
FIG. 9 is a side plan view of the vessel assembly of FIG. 8 at a later stage during deployment of a bridging stent graft in accordance with one embodiment.

FIG. 9 is a side plan view of vessel assembly 700 of FIG. 8 at a later stage during deployment of a second bridging stent graft 902, sometimes called a bridging stent, in accordance with one embodiment. Referring now to FIG. 9, bridging stent graft 902 is located within internal sleeve 106, i.e., within docking channel 132, and the left subclavian artery LSA. More particularly, bridging stent graft 902 self-expands (or is balloon expanded) to be anchored within internal sleeve 106 and the left subclavian artery LSA.

Bridging stent graft 902 includes graft material 904 and one or more circumferential stents 906. Graft material 904 includes any one of the graft materials as discussed above in relation to graft material 112. In addition, circumferential stents 906 are similar or identical to circumferential stents 114 as discussed above.

In one embodiment, bridging stent graft 902 is deployed via supra aortic access. For example, to deploy bridging stent graft 902, a guide wire is introduced through the left subclavian artery LSA, and advanced into distal opening 130 of internal sleeve 106.

A delivery system including bridging stent graft 902 is introduced via supra aortic access and is advanced into the left subclavian artery LSA and internal sleeve 106 over the guidewire. Bridging stent graft 902 is then deployed from the delivery system, e.g., by removal of a sheath constraining bridging stent graft 902.

In one embodiment, a proximal end 908 of bridging stent graft 902 is adjacent or distal of proximal opening 128 of internal sleeve 106. Accordingly, bridging stent graft 902 overlaps the entire length of docking graft 100 insuring good overlap and seal between bridging stent graft 902 and internal sleeve 106. However, in other embodiments, bridging stent graft 902 does not overlap the entire length of docking graft 100, but has sufficient overlap to insure adequate sealing. Bridging stent graft 902 is co-axial with internal sleeve 106 in accordance with this embodiment.

Upon deployment of bridging stent graft 902, blood flow into internal sleeve 106, i.e., proximal opening 128, is bridged and passed into the left subclavian artery LSA through bridging stent graft 902. As bridging stent graft 902 is deploy via supra aortic access, perfusion of the left subclavian artery LSA is immediate and reliable thus minimizing the complexity of the procedure and the associated risks.

Figure 10:
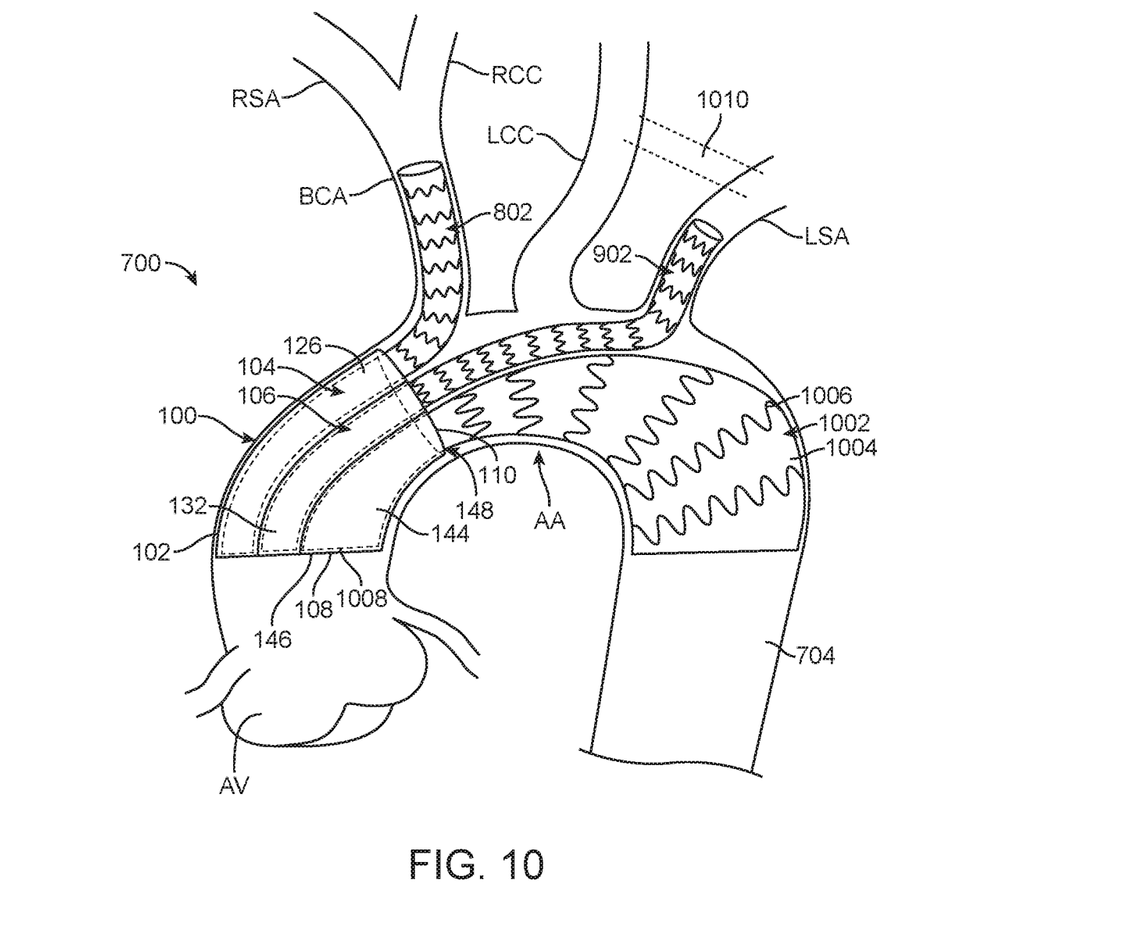
FIG. 10 is a cross-sectional view of the vessel assembly of FIG. 9 at a final stage during deployment of a tube graft in accordance with one embodiment.

FIG. 10 is a cross-sectional view of vessel assembly 700 of FIG. 9 at a final stage during deployment of a tube graft 1002 in accordance with one embodiment. Referring to FIG. 10, tube graft 1002 is deployed into main graft 102 and into aorta 704 and is attached thereto. More particularly, tube graft 1002 is deployed into main docking channel 144 and within main graft 102.

Tube graft 1002 includes graft material 1004 and one or more circumferential stents 1006. Graft material 1004 includes any one of the graft materials as discussed above in relation to graft material 112. In addition, circumferential stents 1006 are similar or identical to circumferential stents 114 as discussed above.

Tube graft 1002 is deployed into main graft 102 and aorta 704, e.g., via femoral access. For example, to deploy tube graft 1002, a guide wire is introduced via femoral access, i.e., is inserted into the femoral artery and routed up through the abdominal aorta, and into distal opening 148 of main docking channel 144, and more generally into distal opening 118 of main graft 102. A delivery system including tube graft 1002 is introduced via femoral access and is advanced into main docking channel 144, and more generally into lumen 120 of main graft 102 over the guidewire. Tube graft 1002 is then deployed from the delivery system, e.g., by removal of a sheath constraining tube graft 1002.

In one embodiment, a proximal end 1008 of tube graft 1002 is adjacent or distal of proximal opening 146 of main docking channel 144 and generally of proximal opening 116 of main graft 102. Accordingly, tube graft 1002 overlaps the entire length of docking graft 100 insuring good overlap and seal between tube graft 1002 and main graft 102, first internal sleeve 104, and second internal sleeve 106. However, in other embodiments, tube graft 1002 does not overlap the entire length of docking graft 100, but has sufficient overlap to insure adequate sealing. Tube graft 1002 is co-axial with main docking channel 144 in accordance with this embodiment.

In one embodiment, internal sleeves 104, 106 are configured to exert a higher radial force than the radial force of tube graft 1002. As used herein, "radial force" includes both a radial force exerted during expansion/deployment as well as a chronic radial force continuously exerted after implantation such that a scaffold has a predetermined compliance or resistance as the surrounding native anatomy, e.g., the aorta 704, expands and contracts during the cardiac cycle. The radial force of tube graft 1002 is configured to be lower than that of internal sleeves 104, 106 to avoid collapse of internal sleeves 104, 106 when tube graft 1002 is deployed against and adjacent thereof and thus maintain perfusion of internal sleeves 104, 106.

To configure internal sleeves 104, 106 and tube graft 1002 with differing relative radial forces, circumferential stents 138, 140 of internal sleeves 104, 106 are constructed with relatively thicker and/or shorter segments of material than circumferential stents 1006 of tube graft 1002. Shorter and/or thicker circumferential stents 138, 140 have less flexibility but greater radial force to ensure that circumferential stents 1006 of tube graft 1002 do not collapse lumens 126, 132 of internal sleeves 104, 106. Other variations or modification of circumferential stents 138, 140, 1006 may be used to achieve relative radial forces in other embodiments.

In another embodiment, bridging stent grafts 802, 902 are configured to exert a higher radial force than the radial force of tube graft 1002. For example, circumferential stents 806, 906 of bridging stent grafts 802, 902 are constructed with relatively thicker and/or shorter segments of material than circumferential stents 1006 of tube graft 1002. Accordingly, bridging stent grafts 802, 902 prevent collapse of internal sleeves 104, 106 when tube graft 1002 is deployed against and adjacent thereof and thus maintain perfusion of internal sleeves 104, 106 including bridging stent grafts 802, 902 therein.

Upon deployment of tube graft 1002, blood flow into proximal opening 146 of main docking channel 144 is bridged and passed into the aorta 704 through tube graft 1002. In this manner, any overlapped diseased regions of the aorta 704 are excluded.

Generally, grafts 802, 902, 1002 are deployed in parallel within docking graft 100. Docking graft 100 forms the foundation, or anchor device, for attachment of grafts 802, 902, 1002 to aorta 704. Grafts 802, 902 are deployed via supra-aortic access after sub selecting each gate. Grafts 802, 902, 1002 extend distally in parallel from docking graft 100. Although various features may be described as parallel, in light of this disclosure, the features may not be exactly parallel due to being deformed by and assuming the shape of aorta 704.

In accordance with this embodiment, tube graft 1002 overlaps, excludes and thus occludes the left common carotid artery LCC. In accordance with this embodiment, a bypass 1010, e.g., a bypass graft, provides perfusion to the left common carotid artery LCC. Illustratively, bypass 1010 provides perfusion of the left common carotid artery LCC from the left subclavian artery LSA.

Bypass 1010 is surgically inserted during the same procedure as deployment of docking graft 100, grafts 802, 902, and tube graft 1002. However, in another embodiment, bypass 1010 is surgically inserted prior to deployment of docking graft 100, grafts 802, 902, and tube graft 1002, e.g., to simplify the procedure.

Figure 11:
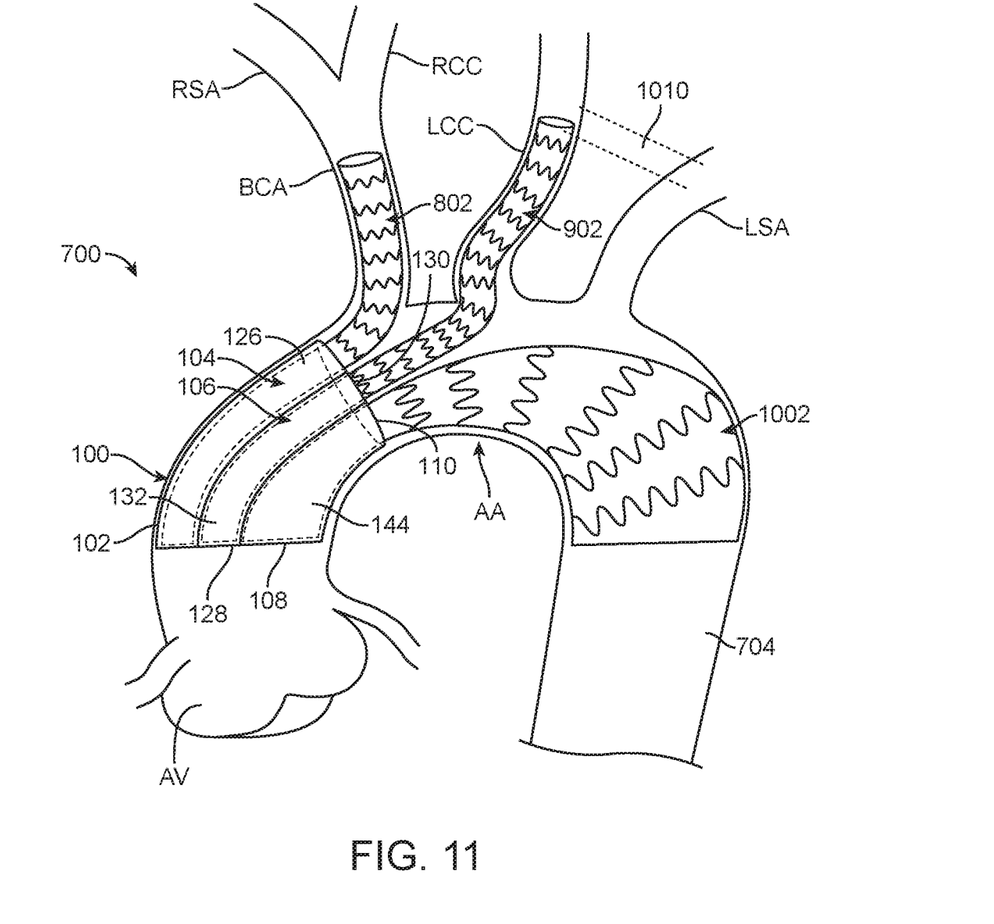
FIG. 11 is a side plan view of the vessel assembly of FIG. 8 at a later stage during deployment of a bridging stent graft in accordance with another embodiment.

FIG. 11 is a side plan view of vessel assembly 700 of FIG. 8 at a later stage during deployment of bridging stent graft 902 in accordance with another embodiment. Vessel assembly 700 of FIG. 11 is similar to vessel assembly 700 of FIG. 10 and only the significant differences are discussed below.

Referring now to FIG. 11, bridging stent graft 902 is located within internal sleeve 106, i.e., within docking channel 132, and the left common carotid artery LCC (in contrast, in FIG. 10, bridging stent graft 902 is located left subclavian artery LSA). More particularly, bridging stent graft 902 self-expands (or is balloon expanded) to be anchored within internal sleeve 106 and the left common carotid artery LCC.

In one embodiment, bridging stent graft 902 is deployed via supra aortic access. For example, to deploy bridging stent graft 902, a guide wire is introduced through the left common carotid artery LCC, and advanced into distal opening 130 of internal sleeve 106.

A delivery system including bridging stent graft 902 is introduced via supra aortic access and is advanced into the left common carotid artery LCC and internal sleeve 106 over the guidewire. Bridging stent graft 902 is then deployed from the delivery system, e.g., by removal of a sheath constraining bridging stent graft 902.

Upon deployment of bridging stent graft 902, blood flow into internal sleeve 106, i.e., proximal opening 128, is bridged and passed into the left common carotid artery LCC through bridging stent graft 902. As bridging stent graft 902 is deploy via supra aortic access, perfusion of the left common carotid artery LCC is immediate and reliable thus minimizing the complexity of the procedure and the associated risks.

Tube graft 1002 is deployed into main graft 102 and into aorta 704 and is attached thereto as discussed above. Tube graft 1002 overlaps, excludes and thus occludes the left subclavian artery LSA. In accordance with this embodiment, bypass 1010 provides perfusion to the left subclavian artery LSA. Illustratively, bypass 1010 provides perfusion of the left subclavian artery LSA from the left common carotid artery LCC.

Figure 12:
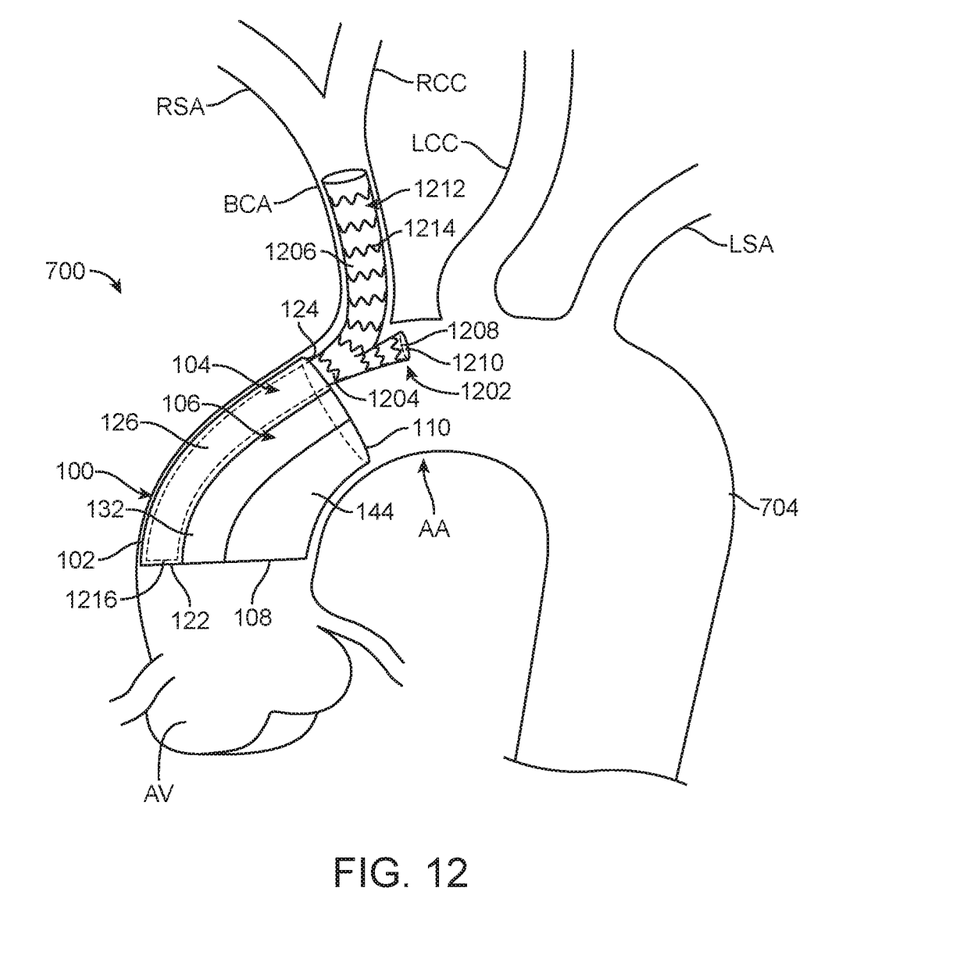
FIG. 12 is a cross-sectional view of the vessel assembly of FIG. 7 at a later stage during deployment of a bifurcated graft in accordance with one embodiment.

FIG. 12 is a cross-sectional view of vessel assembly 700 of FIG. 7 at a later stage during deployment of a bifurcated graft 1202, sometimes called a first bridging stent graft 1202, in accordance with one embodiment. Referring now to FIG. 12, bifurcated graft 1202 includes a main graft 1204 that is bifurcated into first branch graft 1206 and a second branch graft 1208. First branch graft 1206 is longer than second branch graft 1208, sometimes called a contralateral gate.

Main graft 1204 is located within internal sleeve 104, i.e., within docking channel 126, and first branch graft 1206 is located with the brachiocephalic artery BCA. More particularly, main graft 1204 self-expands (or is balloon expanded) to be anchored within internal sleeve 104 and first branch graft 1206 self-expands (or is balloon expanded) to be anchored within the brachiocephalic artery BCA. A distal opening 1210 of second branch graft 1208 is proximal to the left common carotid artery LCC.

Bifurcated graft 1202 includes graft material 1212 and one or more circumferential stents 1214. Graft material 1212 includes any one of the graft materials as discussed above in relation to graft material 112. In addition, circumferential stents 1214 are similar or identical to circumferential stents 114 as discussed above.

In one embodiment, bifurcated graft 1202 is deployed via supra aortic access after sub selecting the gate. For example, to deploy bifurcated graft 1202, a guide wire is introduced through the right subclavian artery RSA, and advanced into distal opening 124 of internal sleeve 104.

A delivery system including bifurcated graft 1202 is introduced via supra aortic access and is advanced into the brachiocephalic artery BCA and internal sleeve 104 over the guidewire. Bifurcated graft 1202 is then deployed from the delivery system, e.g., by removal of a sheath constraining bifurcated graft 1202.

In one embodiment, a proximal end 1216 of bifurcated graft 1202 is adjacent or distal of proximal opening 122 of internal sleeve 104. Accordingly, bifurcated graft 1202 overlaps the entire length of docking graft 100 insuring good overlap and seal between bifurcated graft 1202 and internal sleeve 104. However, in other embodiments, bifurcated graft 1202 does not overlap the entire length of docking graft 100, but has sufficient overlap to insure adequate sealing.

Upon deployment of bifurcated graft 1202, blood flow into internal sleeve 104, i.e., proximal opening 122, is bridged and passed into the brachiocephalic artery BCA through bifurcated graft 1202, i.e., through first branch graft 1204. As bifurcated graft 1202 is deploy via supra aortic access, perfusion of brachiocephalic artery BCA is immediate and reliable thus minimizing the complexity of the procedure and the associated risks.

Figure 13:
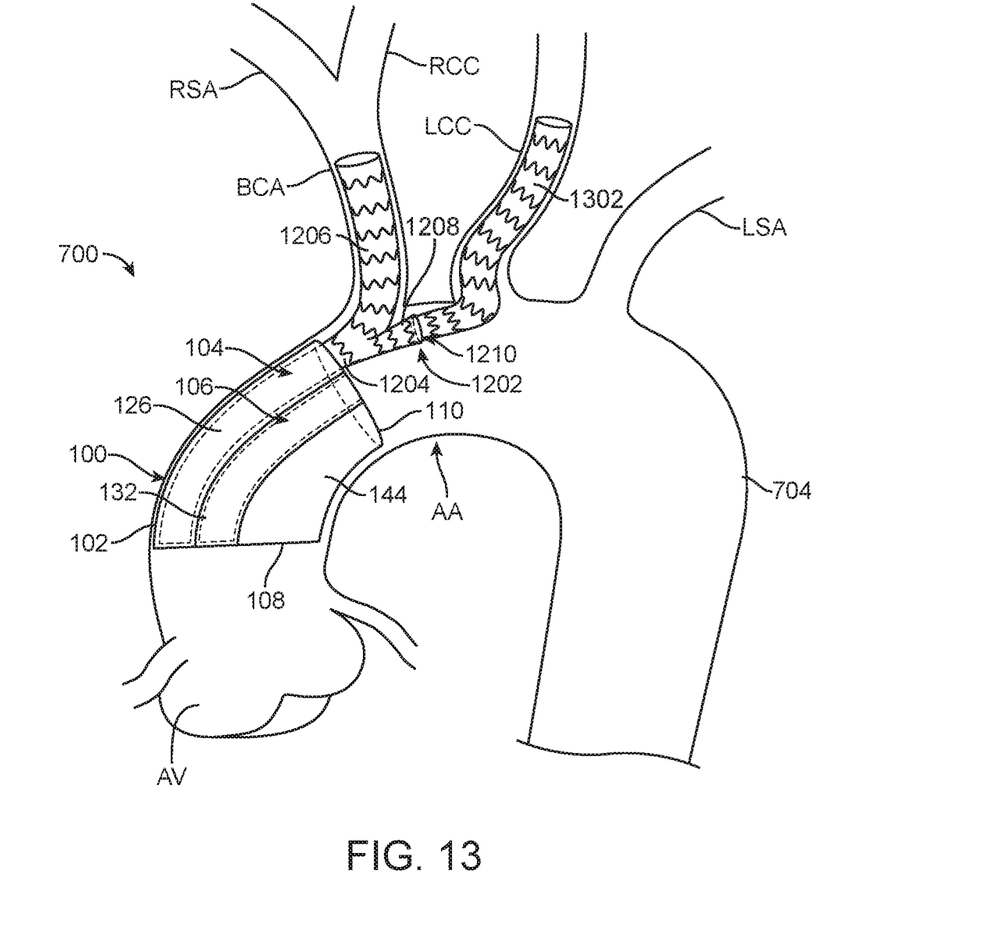
FIG. 13 is a side plan view of the vessel assembly of FIG. 12 at a later stage during deployment of a bridging stent graft in accordance with another embodiment.

FIG. 13 is a side plan view of vessel assembly 700 of FIG. 12 at a later stage during deployment of bridging stent graft 1302 in accordance with another embodiment. Referring now to FIG. 13, bridging stent graft 1302 is located within second branch graft 1208 and the left common carotid artery LCC. More particularly, bridging stent graft 1302 self-expands (or is balloon expanded) to be anchored within second branch graft 1208 and the left common carotid artery LCC.

In one embodiment, bridging stent graft 1302 is deployed via supra aortic access. For example, to deploy bridging stent graft 1302, a guide wire is introduced through the left common carotid artery LCC, and advanced into distal opening 1210 of second branch graft 1208.

A delivery system including bridging stent graft 1302 is introduced via supra aortic access and is advanced into the left common carotid artery LCC and second branch graft 1208 over the guidewire. Bridging stent graft 1302 is then deployed from the delivery system, e.g., by removal of a sheath constraining bridging stent graft 1302.

Upon deployment of bridging stent graft 1302, blood flow into second branch graft 1208 is bridged and passed into the left common carotid artery LCC through bridging stent graft 1302. As bridging stent graft 1302 is deploy via supra aortic access, perfusion of the left common carotid artery LCC is immediate and reliable thus minimizing the complexity of the procedure and the associated risks.

Figure 14:
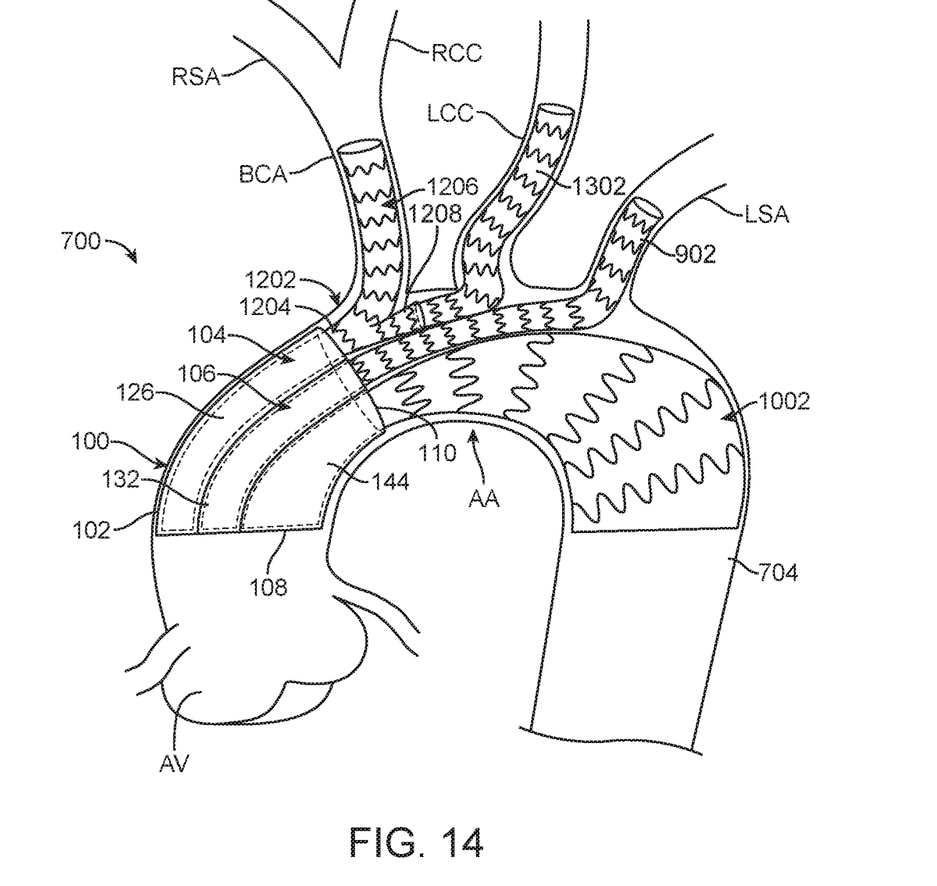
FIG. 14 is a cross-sectional view of the vessel assembly of FIG. 13 at a later stage during deployment of a bridging graft and a tube graft in accordance with one embodiment.

FIG. 14 is a cross-sectional view of vessel assembly 700 of FIG. 13 at a later stage during deployment of bridging stent graft 902 and tube graft 1002 in accordance with one embodiment. Bridging stent graft 902 is located within internal sleeve 106, i.e., within docking channel 132, and the left subclavian artery LSA in a manner similar to that discussed above regarding FIG. 9, and so the discussion is not repeated here for simplicity. Further, tube graft 1002 is deployed into main graft 102 and into aorta 704 in a manner similar to that discussed above regarding FIG. 10, and so the discussion is not repeated here for simplicity.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An assembly comprising:
   a docking graft comprising:
      a main graft defining a main lumen;
      a first internal lumen within the main lumen, the first internal lumen configured to receive a first bridging stent graft therein, the first internal lumen being defined by a first internal sleeve;
      a second internal lumen within the main lumen, the second internal lumen configured to receive a second bridging stent graft therein, the second internal lumen being defined by a second internal sleeve; and
      a main docking lumen within the main lumen, the main docking lumen configured to receive a tube graft therein, the first internal lumen, the second internal lumen, and the main docking lumen being parallel to one another and extending an entire length of the docking graft from a proximal end of the docking graft to a distal end of the docking graft when the docking graft is in a relaxed configuration,
      wherein the main docking lumen has a proximal opening at the proximal end of the docking graft that is defined by an inner surface of the main graft and outer surfaces of the first internal sleeve and the second internal sleeve, and
      wherein the main docking lumen has a distal opening at the distal end of the docking graft that is defined by the inner surface of the main graft and the outer surfaces of the first internal sleeve and the second internal sleeve.

2. The assembly of claim 1,
   wherein the main graft comprises graft material and at least one stent;
   the first internal sleeve comprises graft material and at least one stent; and
   the second internal sleeve comprises graft material and at least one stent.

3. The assembly of claim 1 wherein the first internal sleeve and the second internal sleeve are coupled to the inner surface of the main graft.

4. The assembly of claim 3 further comprising an attachment means coupling the first internal sleeve and the second internal sleeve to the inner surface of the main graft.

5. The assembly of claim 1 wherein the first internal lumen extends from a proximal opening of the first internal sleeve to a distal opening of the first internal sleeve.

6. The assembly of claim 1 wherein the second internal lumen extends from a proximal opening of the second internal lumen to a distal opening of the second internal lumen.

7. The assembly of claim 1 wherein the first internal sleeve has a first diameter equal to a second diameter of the second internal sleeve.

8. The assembly of claim 1 wherein the first internal sleeve is cylindrical and the second internal sleeve is cylindrical.

9. The assembly of claim 1 wherein the first internal sleeve abuts the second internal sleeve along entire lengths of the first internal sleeve and the second internal sleeve.

10. The assembly of claim 1 wherein the first internal lumen is further defined by the main graft, and the second internal lumen is further defined by the main graft.

11. The assembly of claim 1 wherein the main docking lumen is defined by the main graft, the first internal sleeve, and the second internal sleeve.

12. The assembly of claim 1 wherein the main lumen consists of the first internal lumen, the second internal lumen, and the main docking lumen.

13. The assembly of claim 1 further comprising:
    the first bridging stent graft within the first internal lumen;
    the second bridging stent graft within the second internal lumen; and
    the tube graft within the main docking lumen.

14. The assembly of claim 13 wherein the first bridging stent graft, the second bridging stent graft, and the tube graft are parallel to one another within the docking graft and extend distally from the docking graft.

15. The assembly of claim 13 wherein the first bridging stent graft comprises:
   a main graft;
   a first branch graft; and
   a second branch graft, the main graft being bifurcated into the first branch graft and the second branch graft, the assembly further comprising:
   a bridging stent graft within the second branch graft.

* * * * *